United States Patent [19]

Jelly

[11] Patent Number: Plant 5,635

[45] Date of Patent: Jan. 14, 1986

[54] TEA ROSE NAMED JELRAFLOKI

[75] Inventor: Robert G. Jelly, Richmond, Ind.

[73] Assignee: E. G. Hill Co., Inc., Richmond, Ind.

[21] Appl. No.: 610,821

[22] Filed: May 15, 1984

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Charles W. Rummler

[57] ABSTRACT

A new and distinct variety of rose plant of the hybrid tea class particularly distinguished by its bright red double flowers of medium size having a vermilion red color on the inside and a turkish red color on the outside, borne on stems of average size from a plant having a vigorous growth habit with a particularly great aptitude for forcing and an excellent winter aptitude. The flowers of this plant are long lasting when cut and the petals drop off cleanly.

14 Drawing Figures

BACKGROUND OF THE NEW PLANT

This new hybrid tea rose originated as a seeding at Richmond, Ind., resulting from my crossing of two selected genitors with the object of creating a new tea rose variety of a very original red color, especially for the production of cut flowers, having a particular aptitude for forcing and good winter aptitude. The rose plant selected to be the seed parent of this new variety was an unnamed seedling of unknown origin and the pollen parent was chosen to be the variety "Jelvanica" (unpatented) and each of these genitors was selected because previous study of their individual characteristics had indicated that their combination would most likely fulfill the objects of this invention.

The seedlings resulting from this crossing were grown at Richmond, Ind., and selected ones of the lot were grafted and grown and the one plant coming closest to my primary objective was chosen for asexual propagation and study, its double medium sized flowers having a shiny vermilion red inside color and a turkish red outside color. Continued propagation of this plant by "eye" grafting through successive generations at Richmond, Ind., and at Cap d'Antibes, France, has demonstrated that the novel characteristics of the selected seedling hold true from generation to generation and appear to be firmly fixed.

DESCRIPTION OF THE DRAWING

My new variety of tea rose is illustrated by the accompanying full color photographic drawing showing the distinctive elements of the new plant and in which.

DESCRIPTION OF THE NEW PLANT

Figures 1, 2, 3, 4, 5, 6, 7, 8, 9, 10, 11, 12, 13, 14:
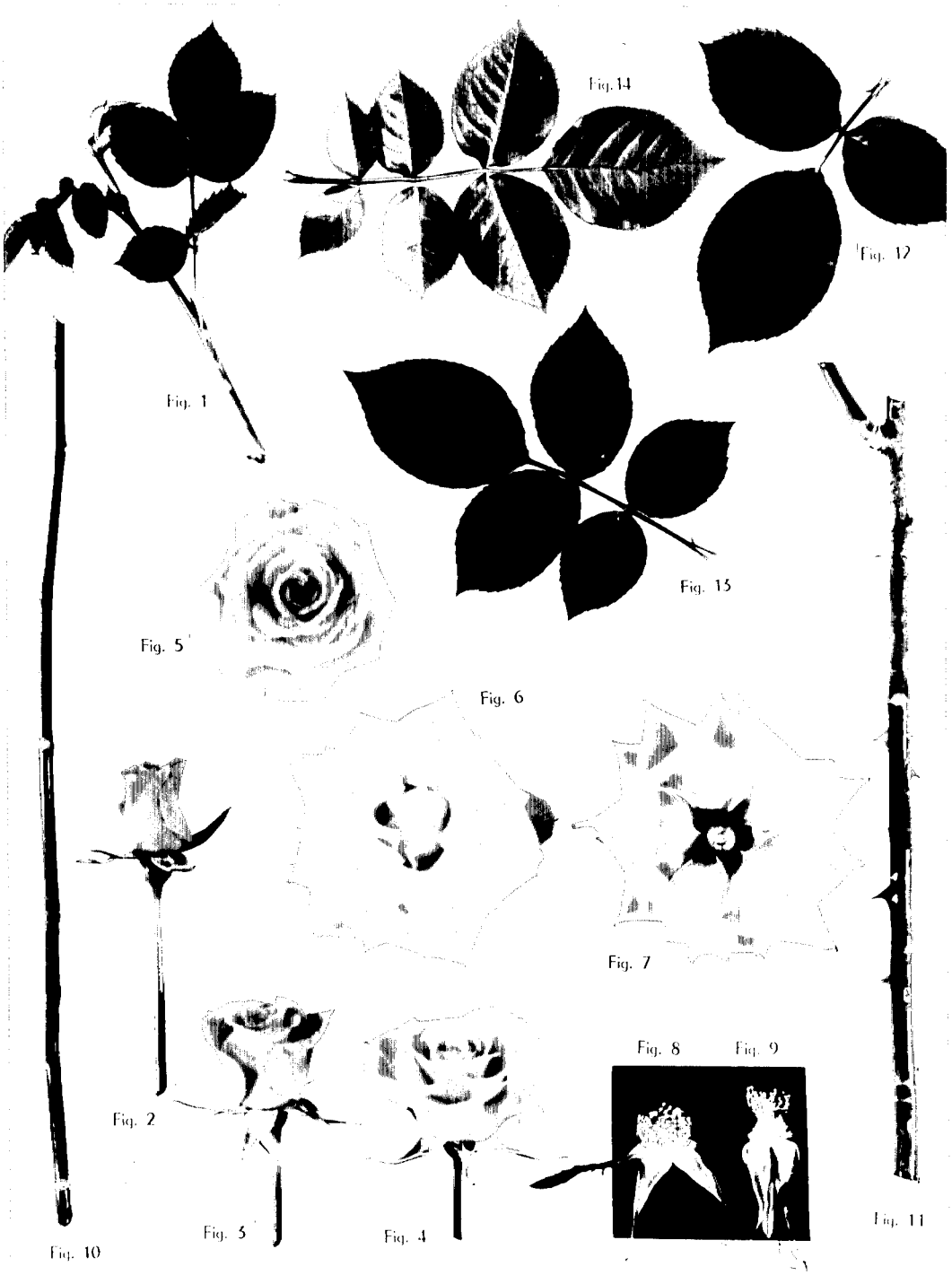
FIG. 1 illustrates a young shoot.
FIG. 2 shows a bud when the sepals burst open.
FIG. 3 shows a bud when the petals first open.
FIG. 4 shows a flower in the course of opening.
FIG. 5 is a face view of a newly opened flower illustrating the inside coloration.
FIG. 6 is a face view of a flower fully blown showing the outside coloration.
FIG. 7 is a rear view of a fully blown flower showing the outside coloration.
FIG. 8 is a view of a floral receptacle showing the disposition of the stamens (the petals having been removed)
FIG. 9 is a view of the floral receptacle showing the disposition of the pistils (the stamens being removed)
FIG. 10 shows a portion of floral stem.
FIG. 11 shows a portion of a main branch.
FIG. 12 is a top side view of a leaf with three leaflets.
FIG. 13 is a top side view of a leaf with five leaflets.
FIG. 14 is an under side view of a leaf with seven leaflets.

The following is a detailed description of my new rose plant as observed on plants being grown in greenhouse at Cap d'Antibes, France, the color designations being according to The R.H.S. Colour Chart of The Royal Horticultural Society of London, England.

THE PLANT

Origin: Seedling.

Parentage:

*Seed parent.*—A selected rose plant of an unnamed variety of unknown origin.

*Pollen parent.*—The rose variety known as "Jelvanica" (unpatented).

Classification: Hybrid tea rose.

Form: An erect bush.

Height: On the basis of cutting back the plants in greenhouse to approximately 85 cm., the length of the flower bearing stems reach a height between 60 and 75 cm.

Growth: Vigorous and upright.

Branches: Normal.

*Young stems.*—Color: Bronze Green 146A more or less smudged reddish.

*Mature wood.*—Color: Bronze Green 146A.

*Prickles.*—Quantity: In small number. Size: Fairly weak. Shape: Upper edge — Straight and slim. Under edge — Concave. Color: On young stems — Reddish. On mature wood — Havana.

Foliage:

*Quantity.*—Moderately ample.

*Form of leaf.*—Odd pinnate.

Leaflets:

*Number.*—3, 5 and more often 7.

*Shape.*—Oval with an acuminate apex and serrated margins of simple and regular character.

*Texture.*—Leathery.

*Color.*—Young Foliage: Upper Surface — Dark Green 147C. Under Surface — Medium Green 148B. Adult Foliage: Upper Surface — Dark Green 147C. Under Surface — Dark Green 148C.

*Stipules.*—Adnate, pectinate, fairly large and linear.

*Petioles.*—Inner Surface: Grooved, reddish brown on young leaves and medium green on adult leaves. Outer Surface: Light green and bearing a few small hooked prickles.

THE BUD

Size: Medium.

Shape: Ovoid when the sepals burst open.

Length: 2.7 cm., outside the calyx, at the opening of the sepals.

Color: When opening:

*Inner surface.*—Gooseberry Red 46A with very shiny aspect.

*Outer surface.*—Cardinal Red 53A. Aspect — Darker and dull.

Sepals:

*Upper surface.*—Tomentous and greenish.

*Inner surface.*—Light green, the outside petals having their edges slightly glandular and slightly appendiculate. Sometimes they bear a reddish median groove.

*Character.*—The sepals turn outwardly and downwardly as the flower develops.

Peduncle:

*Length.*—About 7.5 to 10 cm.

*Character.*—Straight, rigid, very lightly grooved, more or less smudged reddish and lightly tomentous; very seldom bears a few little hooked prickles.

THE FLOWER

Blooming habit: Flowering is continual in greenhouse.

Number of flowers: Usually one per stem. However, in forced cultivation, the first two auxiliary eyes beneath the flower sometimes develop.

Size of bloom: Medium.

*Diameter.*—About 8.5 to 10 cm.

Shape: Parallel sides as bud opens.

Chorisis: Double.

Petalage:

*Number.*—30 on average.

*Arrangement.*—Imbricated.

*Shape.*—Rounded becoming slightly flattened for the outside petals with tiny unguis of yellowish color on both sides.

*Texture.*—Very firm.

*Color.*—Upon opening: Inside Surface — Vermilion Red 44A suffused with Officer's Red 45A and very shiny. Outside Surface — Strawberry Red 46B when newly open. When newly opened: Inside — Vermilion Red 44A. Aspect — Shiny. Outside — Turkey Red 46C. Aspect — Dull. When fully open: Inside — Blood Red 45D in the center becoming Vermilion Red 44A on outside petals. Outside — Delft Pink 46D in the center and Turkey Red 46C on the outside petals. Aspect — Dull.

Fragrance: None.

Persistence: The petals drop off cleanly.

Lasting quality:

*As cut flowers.*—A relatively long time.

REPRODUCTIVE ORGANS

Stamens:

*Number.*—122 on average.

*Anthers.*—Color: Ochre lightly smudged with fuchsine in the center.

*Filaments.*—Short, yellow at base and generally dark fuchsine in color.

Pistils:

*Number.*—80 on average.

*Styles.*—More or less twisted and tomentous with whitish base and fuchsine top.

*Stigmas.*—Yellowish white.

Receptacle: Light green in color; at the dehiscence of the anthers, the receptacle is fairly wide and jug shape in longitudinal section.

As a new industrial product, this new variety of rose plant can be generally characterized by the fact that from the physical point of view, the plant with bronze green adult wood, is erect, the flower is double, coloration is shiny vermilion red on the inside and turkey red outside, the petals are very firm and bear a tiny yellowish unguis on both surfaces. From the biological point of view, this plant has a very vigorous vegetation, a very great aptitude for forcing with excellent winter aptitude, and is not particularly susceptible to cryptogamic diseases; its flowers last a long time when cut and the petals drop off cleanly.

I claim:

1. A new and distinct hybrid tea rose plant, substantially as herein shown and described, particularly distinguished by its double flowers of medium size and bright red coloration, a vigorous growth habit and a very good aptitude for forcing and wintertime culture.

* * * * *